United States Patent [19]

Konig et al.

[11] 4,386,089

[45] May 31, 1983

[54] β-LACTAM ANTIBIOTICS AND THEIR MEDICINAL USE

[75] Inventors: Hans-Bodo Konig; Karl G. Metzger; Michael Preiss, all of Wuppertal, Fed. Rep. of Germany

[73] Assignee: Bayer Aktiengesellschaft, Leverkusen, Fed. Rep. of Germany

[21] Appl. No.: 276,762

[22] Filed: Jun. 24, 1981

Related U.S. Application Data

[63] Continuation of Ser. No. 33,300, Apr. 25, 1979, abandoned.

[30] Foreign Application Priority Data

Apr. 26, 1978 [DE] Fed. Rep. of Germany ....... 2818263

[51] Int. Cl.³ .................. A61K 31/43; A61K 31/545
[52] U.S. Cl. ................................ 424/246; 260/239.1; 424/271; 544/22; 544/27; 544/28
[58] Field of Search ............................ 424/246, 271; 260/239.1; 544/27, 28, 22

[56] References Cited

U.S. PATENT DOCUMENTS

| | | | |
|---|---|---|---|
| 3,998,950 | 12/1976 | Broggi et al. | 544/28 |
| 4,098,888 | 7/1978 | Ochiai et al. | 544/28 |
| 4,107,304 | 8/1978 | Schrock et al. | 544/28 |
| 4,128,724 | 12/1978 | Breuer et al. | 544/28 |
| 4,166,115 | 8/1979 | Takaya et al. | 544/30 |
| 4,178,444 | 12/1979 | Monguzzi et al. | 544/30 |
| 4,231,927 | 10/1980 | Monguzzi et al. | 424/271 |
| 4,267,176 | 5/1981 | Kamiya et al. | 544/27 |

FOREIGN PATENT DOCUMENTS 52-78891 7/1977 Japan .

*Primary Examiner*—Paul M. Coughlan, Jr.
*Attorney, Agent, or Firm*—Sprung, Horn, Kramer & Woods

[57] ABSTRACT

β-Lactam compounds of the formula

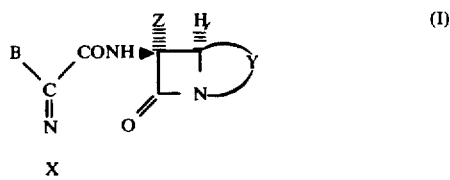

in which
B denotes an optionally substituted heterocyclic 5-membered or 6-membered ring or an optionally substituted phenyl ring,
Z denotes a hydrogen atom or a $C_1$ to $C_4$ alkoxy group,

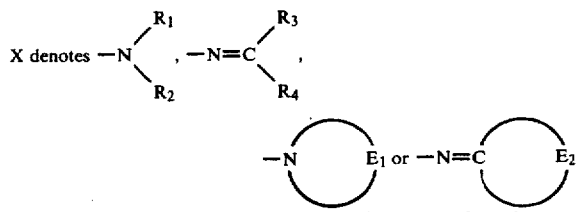

Y, $E_1$ and $E_2$ independently of one another denote a divalent organic radical and
$R_1$, $R_2$, $R_3$ and $R_4$ independently of one another denote a hydrogen atom or an alkyl, alkenyl, alkinyl, alkadienyl, cycloalkyl, cycloalkenyl, cycloalkadienyl, aryl or heterocyclyl radical, it also being possible for the above-mentioned radicals, with the exception of hydrogen, to be substituted, or an acyl radical, are antibacterial agents with a broad antibacterial spectrum and are useful as agents for promoting growth and for improving feed utilization in animals and as antioxidants.

16 Claims, No Drawings

β-LACTAM ANTIBIOTICS AND THEIR MEDICINAL USE

This is a continuation of application Ser. No. 033,300 filed Apr. 25, 1979 now abandoned.

The present invention relates to certain new β-lactam compounds, to a process for their production and to their use as antibacterial agents, as agents for promoting growth and for improving feed utilization in animals and as antioxidants.

β-Lactam compounds which contain the structural element

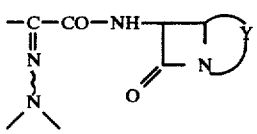

in which

Y has the meaning described below, are mentioned in Japanese Published application No. 5 2078-891, but they contain no further heterocyclic group.

According to the present invention we provide compounds which are β-lactams with a broad antibacterial spectrum, and which correspond to the general formula

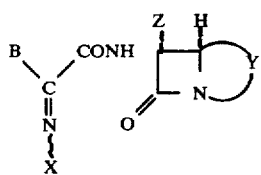 (I)

in which

B denotes an optionally substituted heterocyclic 5-membered or 6-membered ring or an optionally substituted phenyl ring, Z denotes a hydrogen atom or a $C_1$ to $C_4$ alkoxy group,

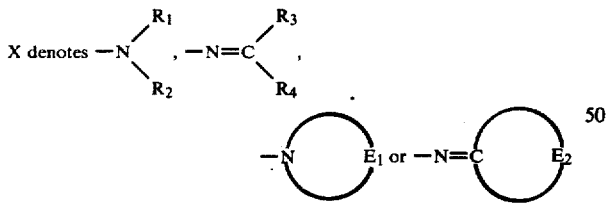

Y, $E_1$ and $E_2$ independently of one another denote a divalent organic radical and $R_1$, $R_2$, $R_3$ and $R_4$ independently of one another denote a hydrogen atom or an alkyl, alkenyl, alkinyl, alkadienyl, cycloalkyl, cycloalkenyl, cycloalkadienyl, aryl or heterocyclyl radical, it also being possible for the above-mentioned radicals, with the exception of hydrogen, to be substituted, or an acyl radical.

Suitable heterocyclic 5-membered and 6-membered radicals B correspond to the formulae

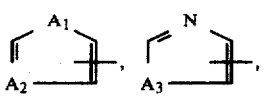

-continued

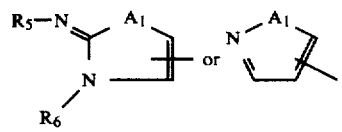

in which
$A_1$ denotes NH, O or S,
$A_2$ denotes CH or N,
$A_3$ denotes CH=CH, CH=N or N=CH and
$R_5$ and $R_6$ independently of each other have one of the meanings given for $R_1$ or together have the meaning given for $E_3$, it being possible for the heterocyclic radicals to contain further substituents, for example amino, alkylamino, dialkylamino, alkyl, hydroxyl, $C_1$ to $C_4$ alkoxy, acylamino or a radical of the formula

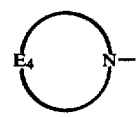

and $E_3$ and $E_4$ independently of each other denote a divalent organic radical.

Suitable optionally substituted phenyl radical B are phenyl unsubstituted or substituted once or twice by hydroxy, amino, chloro, fluoro, methoxy, methyl, acetoxy, acetamino, methylsulfonyloxy, methylsulfonylamino, hydroxysulfonylamino, carboxy or amino carbonyl. Preferred are phenyl, hydroxyphenyl and aminophenyl.

Suitable organic radicals Y correspond, in the form of the free acids, to the formula

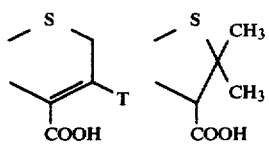

in which T denotes hydrogen, $—E_5—R_7$, $—E_6—R_8$;

in which T denotes hydrogen, $—E_5—R_7$, $—E_6—R_8$;

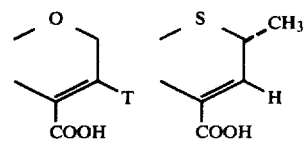

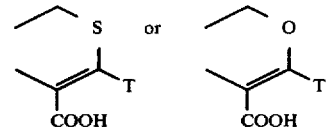

E₅ denotes a bivalent organic radical, preferably $+CH_2+_{1 \text{ to } 4}$, —CH=, —CH=CH—, $+CH_2+_{1 \text{ to } 2}$ CH=CH—, —CH₂—S—CH₂—, —O—, —S—, —NH—, —N—, —CH₂—O—, —CH₂—S—,
                    |
                    R₇

—CH₂—NH— or —CH₂—N— or a direct bond;
                    |
                    R₇

E₆ denotes —(CH₂)₁ to 4; —CH=, —CH=CH—, $+CH_2+_{1 \text{ to } 2}$ CH=CH— or —CH₂—S—CH₂— or a direct bond R₇ denotes hydrogen, optionally substituted alkyl, optionally substituted alkenyl, optionally substituted cycloalkyl, optionally substituted cycloalkenyl, aryl, heterocyclyl; Acyl, Carboxyl or a functional derivative thereof as C₁-C₄-alkoxycarbonyl, aminocarbonyl, cyano or halocarbonyl; formyl, trifluoromethyl, or R₈

R₈ denotes halogen, optionally substituted amino, heterocyclyl attached through N, hydroxy, mercapto, C₁ to C₆-alkyl sulfonyl, C₁ to C₆-alkoxy sulfonyl, C₁ to C₆-alkylamino-sulfonyl, heterocyclylsulfonyl attached through N, C₁ to C₆-alkylsulfinyl, C₁ to C₆-alkoxysulfinyl, di-C₁ to C₆-alkylaminosulfinyl, heterocyclyl sulfinylamino attached through N, C₁ to C₆-alkylthiosulfonyl, optionally substituted hydrazino, optionally substituted hydrazono, optionally substituted hydroxylamino or optionally substituted hydroxylimino

denotes a bivalent heterocyclic radical, attached through N or C which is a mono- or bicyclus, contains from 1 to 5 heteroatoms selected from O, N or S, and may be substituted.

Suitable substituents —E₅—R₇ and —E₆—R₈ are for example hydrogen, methyl, ethyl, 2-ethoxycarbonyl ethyl, 2-phenylethyl, 4-aminocarbonylbenzyl, 2-acetyl-2-ethoxycarbonylethyl, carboxy, aminocarbonyl, acetyl, cyano, formyl, oximinomethyl, 2-methylthio-ethyl, 1-bromoethyl, chloro, hydroxy, methoxy, formyloxy, acetoxy, methylsulfonyloxy, 2,1,3-thiadiazol-4-yloxy, amino, acetylamino, morpholin-1-yl, dimethylamino, methylsulfonylamino, methylthio, methylsulfinyl, methylsulfonyl, 5-methyl-1,3,4-thiadiazol-2-thio, phenylthio, trifluoromethyl, difluoromethyl, hydroxymethyl, formyloxymethyl, acetoxymethyl, aminocarbonyloxymethyl, tert.-butyl carbonyloxymethyl, methoxymethylcarbonyloxymethyl, aminomethylcarbonyloxymethyl, methoxymethyl, allyloxymethyl, phenoxymethyl, dimethylaminomethyliminocarbonyloxymethyl, formylaminocarbonyloxymethyl, ureidocarbonyloxymethyl, (3-hydroxy-4-carboxyphenyl)aminocarbonyloxymethyl, (2-carboxyphenyl)-carbonyloxymethyl, 2-ethoxycarbonylaminophenyl)-carbonyloxymethyl, (2-ethoxycarbonylaminosulfonyl-phenyl-)-carbonyloxymethyl, acetylmethylcarbonyloxymethyl, (2-carboxyethyl)-carbonyloxymethyl, α-hydroxybenzylcarbonyloxymethyl, [1-(4-chlorophenyl-thio)-2-carboxyethyl]-carbonyloxymethyl, 1,3-thiadiazol-2-ylcarbonylthiomethyl, 2,1,3-oxadiazol-4-yl-carbonylthiomethyl, (4-sulphophenyl)-thiomethyl, pyrolidine-1-yl-thiocarbonylthiomethyl, sodiumthiosulphatomethyl, ethoxythiocarbonylthiomethyl, (4-methylpiperazine-1-ylthiocarbonylthiomethyl, methylthiomethyl, isopropylcarbonylthiomethyl, sulphomethyl, 1,2,3,4-oxatriazol-5-yl-methylthiomethyl, vinyl, 1-ethoxycarbonylvinyl, 3-hydroxypropenyl, 3-acetoxypropenyl, 3-aminocarbonyloxypropinyl, 3-(2-methyl-1,3,4-thiadiazol-5-ylthio)-propanyl, cyanomethyl, carboxymethyl, methoxycarbonylmethyl, aminocarbonylmethyl, dimethylaminocarbonylmethyl, (4-methylpiperazine-1-yl)methyl, acetylmethyl,

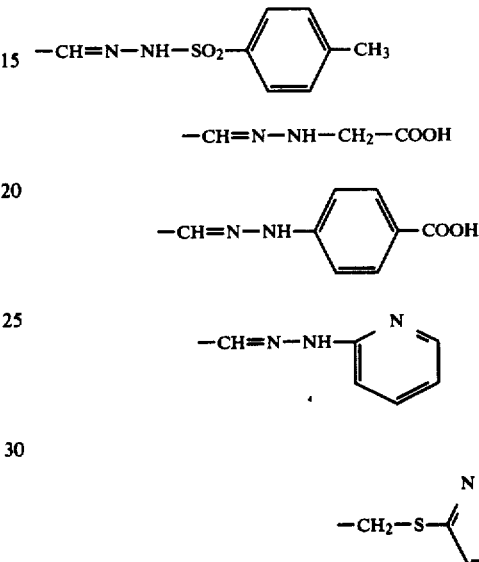

Suitable substituents

are for example:

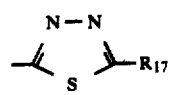

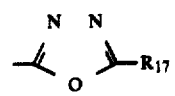

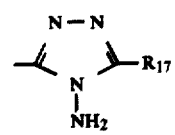

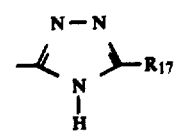

wherein R₁₇ is hydrogen, methyl, aminocarbonylmethylthio, 2-hydroxyethylthio or 2-dimethylaminoethylthio

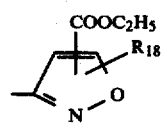

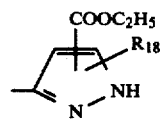

wherein
R$_{18}$ is ethoxycarbonyl, 4-methylphenylsulphonyl, cyano- or phenyl

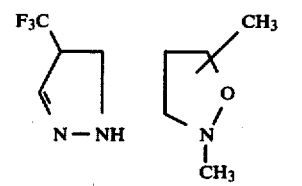

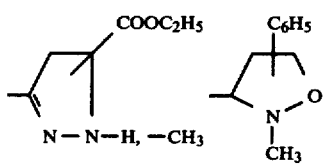

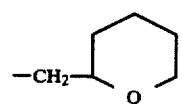

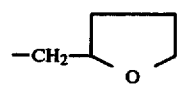

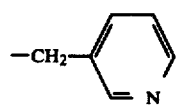

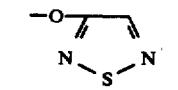

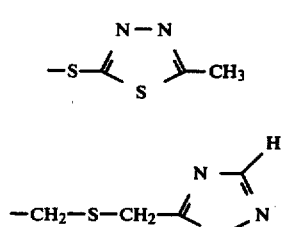

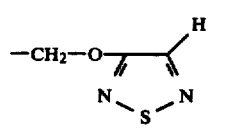

-continued

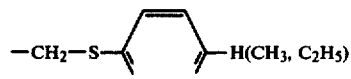

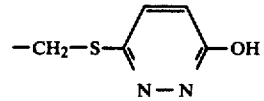

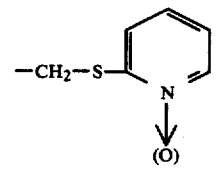

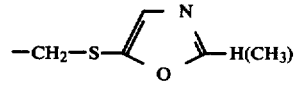

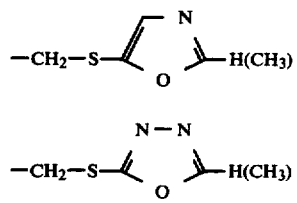

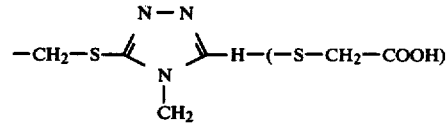

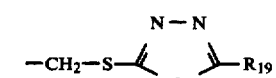

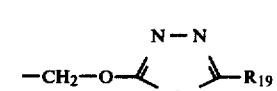

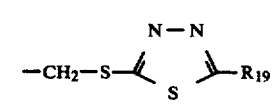

wherein R$_{19}$ is hydrogen, methyl, aminomethyl, acetylaminomethyl, guanidinocarbonylaminomethyl, methylaminocarbonylaminomethyl, methylsulphonylaminomethyl, 2-aminoethyl, 2-ureidoethyl, 2-carbonylvinyl, carbonylmethylthio, sulpho, aminosulfonyl, acetylamino, methylsulfonylamino, 4-pyridino, 2-dimethylaminoethylthio, 2-hydroxyethylthio, aminocarbonylmethylthio, or 2-carboxyethylcarbonylamino.

Suitable substituents

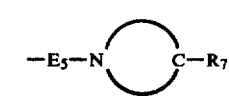

are for example:

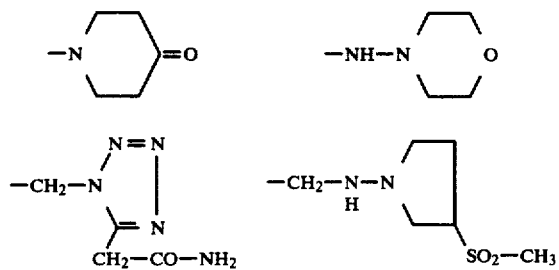

Suitable substituents are for example:

wherein R₂₀ is hydrogen, methyl, 2-dimethylaminoethyl, carboxymethyl, ethoxycarbonylmethyl, aminocarbonylmethyl or sulphomethyl wherein R₂₁ is hydrogen, methyl, ω-carboxy-C₁–C₄ alkyl, sulphomethyl, 2-aminoethyl, 2-dimethylaminoethyl or ω-sulphoamino-C₂–C₅-alkyl A suitable radical is for example Suitable radicals are for example -continued

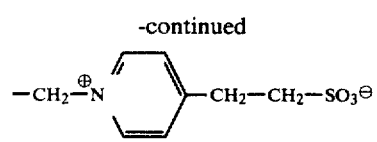

Examples of suitable radicals E₁ are —(CO)$_m$—(NR$_9$-)$_m$—(CH$_2$)$_n$—, —(CH$_2$)$_m$—R$_{10}$—(CH$_2$)$_m$—, —(CO)-$_m$—(CH$_2$)$_p$—, —(CO)$_{2-m}$—(CH$_2$)$_n$—(CO)$_m$—, —CO—CH=CH—CO—, —CO—O—(CH$_2$)$_q$—, —CO—S—(CH$_2$)$_q$—, —CO—NR$_9$—CO—(CH$_2$)$_m$—, —SO$_2$—(CH$_2$)$_p$—, —CO—(CH$_2$)$_q$—SO$_2$—, —CO—NR$_9$—N—CH—, —(CH=CH)$_2$—, —CO—NH—N=CH—CO— or —CO—(CH=CH)$_2$—, in which R$_9$ has any of the meanings given for R$_1$ or denotes

R$_{10}$ denotes O, S, SO, SO$_2$ or NR$_{11}$,

R$_{11}$ denotes a hydrogen, methyl, ethyl, cyclopropyl, methylsulphonyl or furylideneamino, m is 1 or 2, n is 2 or 3, p is 3, 4 or 5 and q is 2, 3 or 4.

Suitable radicals E$_2$ form, with the carbon atom, for example, 4- to 7-membered carbocyclic or heterocyclic rings, the heterocyclic rings containing 1 or 2 heteroatoms from the series O, S or N.

Examples of suitable radicals E$_3$ are 2-membered or 3-membered bridges, the bridge members of which can be carbon atoms or nitrogen atoms, which are optionally substituted by methyl, ethyl, cyclopropyl, methylsulphonyl, furylideneamino, hydroxyl, oxo or amino.

Examples of suitable radicals E$_4$ are —CO—(CH$_2$)$_3$—CO—(CH$_2$)$_4$—, —CONR$_{12}$—(CH$_2$)$_2$—, —CONR$_{12}$—(CH$_2$)$_3$—, —(CO)$_2$—NR$_{12}$—(CH$_2$)$_2$— or —(CH$_2$)$_2$—R$_{10}$—(CH$_2$)$_2$—, wherein R$_{12}$ denotes hydrogen, methyl, ethyl, cyclopropyl, methylsulphonylamino or furylideneamino and R$_{10}$ has the meaning already given.

Alkyl R$_1$, R$_2$, R$_3$, R$_4$ or R$_7$ as a substituent of B, in the definition alkyl, alkylamino or dialkylamino is, in particular, C$_1$ to C$_4$ alkyl, preferably methyl and ethyl, which can be substituted by aryl, heterocyclyl, halogen, in particular chlorine and bromine, hydroxyl, C$_1$ to C$_4$ alkoxy, acyloxy or acylamino. Alkenyl and alkinyl R$_1$, R$_2$, R$_3$, R$_4$ and R$_7$ contain, in particular, 2 to 4 carbon atoms.

Alkadienyl, cycloalkenyl and cycloalkadienyl R$_1$, R$_2$, R$_3$, R$_4$ and R$_7$ contain, in particular, 5 to 7 carbon atoms. Cycloalkyl R$_1$, R$_2$, R$_3$ and R$_4$ is, in particular, C$_3$ to C$_6$ cycloalkyl, preferably cyclopropyl.

Aryl R$_1$, R$_2$, R$_3$, R$_4$ and R$_7$ and as a substituent of the alkyl radicals R$_1$ to R$_4$ is, in particular, phenyl which is substituted by C$_1$ to C$_4$ alkyl, C$_1$ to C$_4$ alkoxy or halogen, preferably chlorine or bromine.

Heterocyclyl R$_1$, R$_2$, R$_3$, R$_4$ and R$_7$ and as a substituent of the alkyl radicals R$_1$ to R$_4$ is, in particular, thienyl, thiazolyl, pyridyl, pyrrolidin-2-on-1-yl, imidazolidin-2-on-1-yl, imidazolidin-2-on-1-yl which is substituted in the 3-position by CH$_3$, C$_2$H$_5$, cyclopropyl, mesyl, acetyl, methylaminosulphonyl or furylideneamino, or piperazine-2,3-dion-1-yl.

Acyl R$_1$, R$_2$, R$_3$, R$_4$ and R$_7$, in the meaning of acylamino as a substituent of B or of the alkyl radicals R$_1$ to R$_4$, and in the meaning acyloxy as a substituent of the alkyl radicals R$_1$ to R$_4$ corresponds, in particular, to the formula

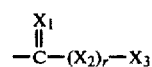

wherein

X$_1$ and X$_2$ independently of one another denote O, S or N-X$_3$,

X$_3$ denotes C$_1$ to C$_4$ alkyl, C$_3$ to C$_7$ cycloalkyl, C$_2$ to C$_4$ alkenyl, aryl or heterocyclyl and r denotes 0 or 1, aryl and heterocyclyl having the meaning already known, or the formula

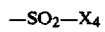

wherein

X$_4$ denotes C$_1$ to C$_4$ alkyl, phenyl, NH$_2$, mono- or di-alkylamino or hydroxyl.

The compounds of the formula I can be in the form of a free acid, a salt, in particular the sodium salt, an inner salt or an ester. The =N~X bond can be in the syn-position

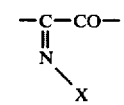

or in the anti-position

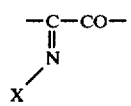

Preferred compounds correspond to the formula II

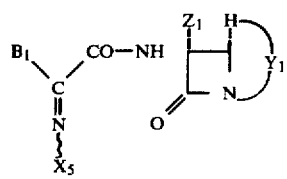

(II)

wherein

Y$_1$, in the form of the free acid, denotes a radical of the formula

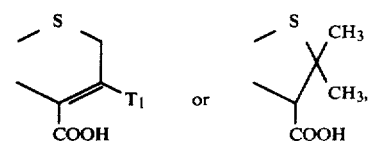

T$_1$ denotes —CH$_2$—O—CO—CH$_3$, —CH$_2$—O—CO—NH$_2$,

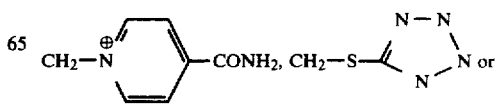

-continued

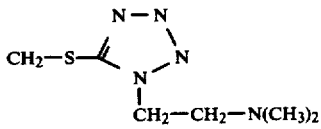

$Z_1$ denotes a hydrogen atom or a methoxy group,
$B_1$ denotes a radical of the formula

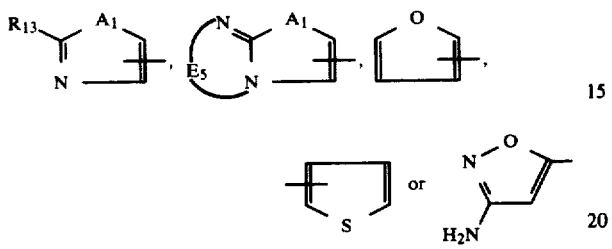

$X_5$ denotes

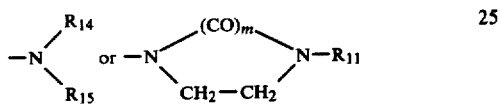

$R_{11}$ denotes a hydrogen atom or a methyl, ethyl, cyclopropyl, methylsulphonyl or furylideneamino radical, $R_{13}$ denotes a hydrogen atom or an amino, $C_1$ to $C_4$ alkylamino, di $C_1$ to $C_4$ alkylamino, ($C_1$ to $C_4$ alkyl)-carbonylamino, piperidino, morpholino, thiomorpholino, piperazino, 4-$C_1$ to $C_4$ alkylpiperazino, 4-oxothiomorpholino or 4,4-dioxothiomorpholino radical, $R_{14}$ denotes a hydrogen atom or a $C_1$ to $C_4$ alkyl, benzyl, phenethyl, cyclohexyl or phenyl radical or a heterocyclic radical of the formula

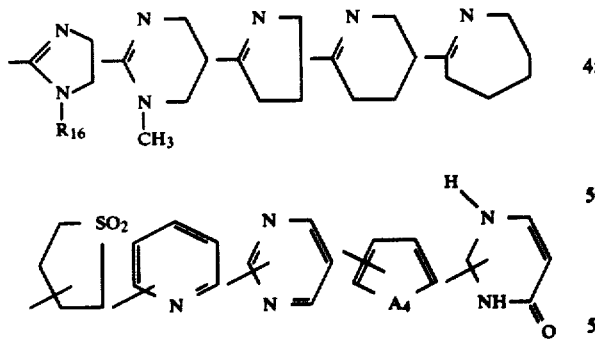

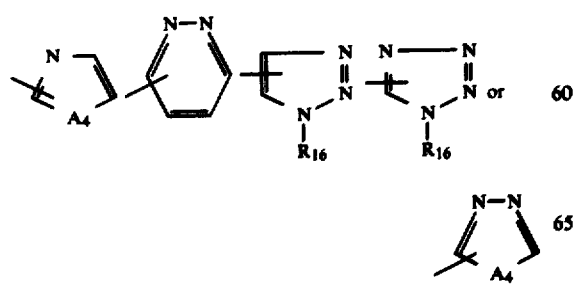

$R_{16}$ denotes a hydrogen atom or a $C_1$ to $C_4$ alkyl, hydroxyethyl or $C_1$ to $C_4$ alkoxyethyl radical, $A_4$ denotes O or S, $R_{15}$ denotes a hydrogen atom or a $C_1$ to $C_4$ alkyl, ($C_1$ to $C_4$ alkyl)-carbonyl or phenylcarbonyl radical, $E_5$ denotes —$CH_2$—$CH_2$—, —$CH_2$—$CH_2$—$CH_2$—, —CH=CH—, —CH=CH—CO—, —CO—CH=CH—, —CO—$CH_2$—$CH_2$—, —$CH_2$—$CH_2$—NH— or —NH—$CH_2$—$CH_2$—, it being possible for the CH and $CH_2$ radicals to be substituted by OH or $NH_2$, and m is 1 or 2.

Very particularly preferred compounds correspond to the formula III

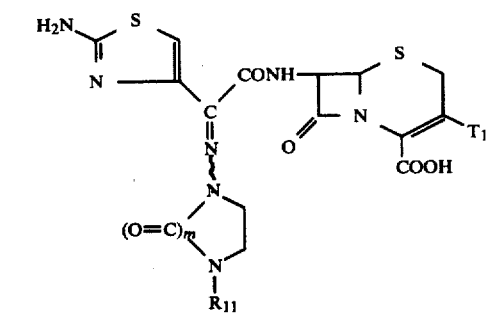

wherein $T_1$, $R_{11}$ and m have the meaning already given.

The particular syn- and anti-forms of one and the same substance are as a rule substances of different activity. Depending on the preparation route and, if, appropriate, on the nature of the protective groups, the syn- or anti-form or a mixture of the two forms, optionally with predominant proportions of one form compared with the other form, can preferentially be obtained. It is also possible to partly or completely convert one form into the other, Lewis acids or proton acids having proved particularly suitable. The syn- and anti-forms also differ in their spectra (for example NMR and IR) and in the Rf values in thin layer chromatography. It is therefore also possible to separate the two forms from one another preparatively by chromatographic processes.

The compounds according to the invention are obtained by a number of different processes, the process steps being in themselves the same but being carried out in a different sequence. It has been found that the two process variants which follow are the most appropriate. In process (1), the compounds of the formula IV

(IV)

wherein

R denotes hydrogen or $C_1$ to $C_4$ alkyl and

U denotes B, a group B protected by one or more protective groups or a chemical precursor of B, is reacted, if necessary after alkaline saponification of the ester group, with compounds of the formula V

$H_2N$—X   (V)

wherein

X has the meaning already indicated, and then, after activating the carbonyl group, for example by reaction with chloroformic acid alkyl esters, the products are reacted with compounds of the formula VI

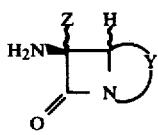
(VI)

wherein

Y and Z have the abovementioned meaning.

If appropriate, splitting off of the protective groups or conversion of the chemical precursor U into the radical B follows.

According to process (2), the compound IV is reacted with the compound VI, for example in the presence of an agent which splits off water and a base. Thereafter, in any desired sequence, the radical B is freed from protective groups or prepared from the precursor U, if necessary, and the reaction with the compound V is carried out.

It as furthermore been found that the compounds of the formula I can also be obtained when compounds of the general formula I in which T denotes —CH$_2$—O—CO—lower alkyl, in particular —CH$_2$—O—CO—CH$_3$, are reacted with nucleophiles, for example with

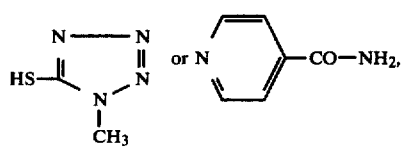

Compounds of the formula I are also obtained when compounds of the general formula I in which T denotes —CH$_2$OH are reacted with O=C=N—SO$_2$Cl or O=C=N—CO—CCl$_3$, the —SO$_2$—Cl or —CO—CCl$_3$ group is then split off and, if appropriate, protective groups are removed. The radical T (—CH$_2$OH) is converted into the radical T=CH$_2$—O—CO—NH$_2$ in a manner which is in itself known.

Compounds of the formula I can also be obtained when compounds of the formula I in which Z denotes hydrogen and which are in the form of the free acids, the salts or esters which can be split, are reacted with a hypochlorite, for example (CH$_3$)$_3$C—O—Cl, in the presence of a methanolate, for example Li—O—CH$_3$, and, if appropriate, protective groups are removed.

Compounds of the general formula I which are in the syn-form can also be obtained when carboxylic acids of the formula VII, in the syn-form

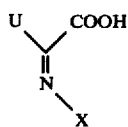
(VII)

are converted into intermediate compounds of the general formula VIII

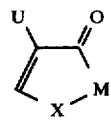
(VIII)

wherein

M denotes O, S or NH.

For this reaction, it is necessary for an oxygen, nitrogen or sulphur atom in the radical X to be in a position such that the carboxyl group of the carboxylic acid VII can react with it in accordance with an intramolecular cyclisation reaction, if appropriate after activation.

A further prerequisite is that the carboxyl group of the carboxylic acid VII in the intermediate compound VIII is present in a sufficiently activated form. The intermediate compound VIII does not have to be capable of isolation or isolated.

By reacting the intermediate compound VIII with the amino compound VI, the compound of the general formula I is then obtained in the syn-form.

The compounds according to the invention exhibit a broad antibacterial spectrum against Gram-positive and Gram-negative germs, in particular against Enterobacteriaceae, above all against those with $\beta$-lactamase forming action.

Furthermore, the compounds according to the invention improve the growth and feed utilisation in animals and can be used as antioxidants.

The active compounds according to the invention display a powerful and broad antimicrobial activity, coupled with low toxicity. These properties enable them to be used as chomotherapeutic active compounds in medicine and as substances for preserving inorganic and organic materials, especially organic materials of all kinds, for example polymers, lubricants, paints, fibres, leather, paper and timber, and foodstuffs and water.

With the aid of the active compounds according to the invention, it is possible to combat Gram-negative and Gram-positive bacteria and bacteria-like microorganisms and to prevent, alleviate and/or cure diseases caused by these pathogens.

The active compounds according to the invention are particularly active against bacteria and bacteria-like micro-organisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermis* and *Staph. aerogenes* (Staph.=Staphylococcus); Lactobacteriaceae, such as Streptococci, for example *Streptococcus pyogenes*, α- and β-*Haemolysing Streptococci*, non-(γ-)-haemolysing Streptococci, *Str. viridans, Str. faecalis* (Enterococci), *Str. agalactiae, Str. lactis* and *Str. anaerobis*, and *Diplococcus pneumoniae* (Pneumococci) (Str.=Streptococcus); Neisseriaceae, such as Neisseriae, for example *Neisseria gonorrhoeae* (Gonococci), *N. meningitidis* (Meningococci), *N. catarrhalis* and N. flava (N=Neisseria); and Corynebacteriaceae, such as Corynebacteria, for example *Corynebacterium diphtheriae, C. pyogenes, C. diphtheroides, C. acnes, C. parvum,*

C. bovis, C. renale, C. ovis and C. murisepticum (C = Corynebacterium).

Enterobacteriaceae, such as Escherichiaebacteria of the Coli group: Escherichia bacteria, for example Escherichia coli, Enterobacter bacteria, for example E. aerogenes and E. cloacae, Klebsiella bacteria, for example K. pneumoniae, and Serratia, for example Serratia marcescens (E. = Enterobacter) K. = Klebsiella), Proteae bacteria of the Proteus group: Proteus, for example Proteus vulgaris, Pr. morganii, Pr. rettgeri and Pr. mirabilis, and Providencia, for example Providencia sp., (Pr. Proteus), and Salmonelleae: Salmonella bacteria, for example Salmonella paratyphi A and B, S. typhi, S. enteritidis, S. chlorerae suis and S. typhimurium (S. = Salmonella), and Shigella bacteria, for example Shigella dysenteriae. Sh. flexneri and Sh. sonnei (Sh. = Shigella);

Pseudomonadaceae, such as Pseudomonas bacteria, for example Pseudomonas aeruginosa, Parvobacteriaceae, such as Pasteurella bacteria, for example Pasteurella multocida, Haemophilus bacteria, for example Haemophilus influenzae, Bacteroidaceae, such as Bacteroides bacteria, for example Bacteroides fragilis, Bacillaceae, such as aerobic spore-forming Bacillaceae, for example Bacillus anthracis, B. subtilis and B. cereus (B. = Bacillus), and anaerobic spore-forming Clostridia, for example Clostridium perfringens (Cl. = Clostridium).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators; e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 500 mg to 2.5 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, such as intravenously or intramuscularly. Preferred pharmaceutical compositions and medicaments are therefore those adapted for administration such as oral or parenteral administration. Administration in the method of the invention is preferably oral or parenteral administration.

In general it has proved advantageous to administer amounts of from 5 mg to 1,000 mg/kg, preferably 10 mg to 150 mg/kg, of body weight per day to achieve effective results. An individual administration preferably contains the active compound or compounds according to the invention in amounts of about 1 to about 250, in particular 10 to 50, mg/kg of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

When used as feed additives, the new compounds can be administered in the customary concentrations and formulations together with the feed or with the feed formulations or with the drinking water. By this means, it is possible to prevent, alleviate and/or cure an infection by Gram-negative or Gram-positive bacteria and also to achieve promotion of growth and better utilisation of the feed. The present invention thus provides a medicated fodder comprising a compound of the invention and a nutritious material.

The new $\beta$-lactam antibiotics are distinguished by powerful antibacterial actions, which have been tested in vivo and in vitro.

In order to broaden the spectrum of action and to achieve a more powderful action, the $\beta$-lactam antibiotics according to the invention can also be combined with aminoglycoside antibiotics, such as gentamicin, kanamicin, sisomicin, amikacin and tobramicin, and lactamase inhibitors, such as clavulanic acid and clavulanic acid derivatives.

The activity of the $\beta$-lactam antibiotics according to the invention can be demonstrated, by way of example, by the following in vitro experiments:

1. In vitro experiments

The compounds from examples 5 and 9, which can be regarded as typical representatives of the compounds according to the invention were diluted to a content of 100 $\mu$g/ml with Müller-Hinton nutrient broth. 0.1% of glucose being added. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates action. At a dosage of 100 $\mu$g/ml, the following bacterial cultures were free from turbidity (sp.=species):

Klebsiella pneumoniae; Enterobacter aerogenes sp.; Providencia; *Serratia marcescens; E. coli* N; Salmonella sp.; *Shigella s.;* Proteus, indole-negative and indole-positive; *Staphylococcus aureus* 133; *Diplococcus pneumoniae* sp.; *Streptococcus pyogenes* W.; Enterococcus sp.; and *Pseudomonas aeruginosa* sp.

The following Examples 4, 5, 8 to 12, 17, 18, 19, 22 and 23, illustrate the preparation of compounds of the invention and the remaining Examples illustrate the preparation of precursors.

EXAMPLE 1

2-(2-tert.-Butoxycarbonylimino-4-thiazolin-4-yl)-glyoxylic acid ethyl ester 13.9 g of di-tert.-butyl pyrocarbonate are added dropwise to 10 g of 2-(2-aminothiazol-4-yl)-acetic acid ethyl ester in 30 ml of tert.-butanol at 45° C. After the reaction has ended (thin layer chromatogram), the solvent is stripped off and the residue is taken up in ether. After washing the ether mixture with dilute hydrochloric acid, drying and concentrating, the residue is crystallised by triturating with petroleum ether (melting point after chromatography: 78°–79° C.). 2.7 g of this substance are boiled unde reflux for 16 hours with 2.1 g of selenium dioxide in 50 ml of dioxane containing 1 ml of water. The mixture is then concentrated on a rotary evaporator, the residue is treated with water and ethyl acetate, the organic phase is concentrated on a rotary evaporator and the residue is triturated with petroleum ether.

Yield: 1.1 g
Melting point: 125° C.
NMR (100 MHz; δ in CCl$_4$): 8.06 (s; thiazoline 5-H)

EXAMPLE 2

2-(2-tert.-Butoxycarbonylimino-4-thiazolin-4-yl)-glyoxylic acid 3.3 g of the substance prepared according to example 1 are dissolved in 15 ml of ethanol. A solution of 0.4 g of sodium hydroxide in 15 ml of water is added to this solution and the mixture is then stirred at 20° C. for 1 hour. The mixture is then evaporated in vacuo, the residue is dissolved in water, this aqueous solution is washed with ethyl acetate and acidified to pH 1.5 with dilute hydrochloric acid and the precipitate which has separated out is filtered off, washed with water and dried.

Yield: 1.4 g.
Melting point: about 150° C. (decomposition)
According to the thin layer chromatogram, the substance is a single compound. NMR (100 MHz; δ in d$_6$-DMSO-CDCl$_3$): 8.24 (s, thiazoline 5-H); 1.44 (s, (CH$_3$)$_3$C).

EXAMPLE 3

2-(2-tert.-Butoxycarbonylimino-4-thiazolin-4-yl)-N-(imidazolidin-2-on-1-yl)-2-iminoacetic acid.

0.7 g of 1-amino-2-oxoimidazolidine is dissolved in 5 ml of ethanol under the influence of heat. 1.9 g of the substance prepared according to example 2 are added to this solution and the mixture is then stirred at 20° C. overnight. The precipitate is filtered off, washed with ethanol and dried.

Yield: 1.3 g.
Melting point: about 198° C. (decomposition)
NMR (100 MHz; δ in d$_7$-DMF/CD$_3$OD): 7.34 (s; thiazoline 5-H); 3.42 ("s"; —CH$_2$—CH$_2$—); and 1.52 (s; (CH$_3$)$_3$C).

The substance still contains about 0.4 molar equivalent of ethanol.

EXAMPLE 4

7-[2-(2-tert.-Butoxycarbonylimino-4-thiazolin-4-yl)-N-(imidazolidin-2-on-1-yl)-2-iminoacetamido]-3-acetoxymethyl-3-cephem-4-carboxylic acid

Mixture A 3.0 g of the substance prepared according to example 3 are suspended in 40 ml of methylene chloride. 1.2 ml of triethylamine are then added at 20° C. The mixture is stirred for about 10 minutes and then cooled to −40° C., and 0.05 ml of 3-dimethylaminopropanol and 0.81 ml of chloroformic acid ethyl ester are added successively to the solution. The mixture is stirred at −35° C. for a further 20 minutes and 40 ml of acetone, which has been pre-cooled to −35° C., are added.

Mixture B 3.0 g of 7-aminocephalosporanic acid are suspended in 20 ml of water and are dissolved by adding just the amount of 1 N sodium hydroxide solution required. 20 ml of acetone are added and the mixture is cooled to −10° C.

Mixture B is added to mixture A, whilst stirring, and the resulting mixture is stirred at a room temperature of 20° C. for 3 hours. It is then diluted with a large amount of water, ethyl acetate is added, the mixture is shaken thoroughly and a small amount of undissolved material is filtered off. The aqueous phase is separated off and and extracted again with ethyl acetate. The aqueous phase, which has been separated off again, is then covered with a fresh layer of ethyl acetate and acidified to pH 1.5 with dilute hydrochloric acid, whilst stirring. The ethyl acetate phase is separated off, washed with a little water, dried over magnesium sulphate and concentrated in vacuo. A precipitate (precipitate 1) thereby separates out and is filtered off (2.0 g). The filtrate obtained after filtering off this precipitate is evaporated completely in vacuo (residue: 1.5 g). Both substances are dissolved or suspended separately in methylene chloride and the solution or suspension is left to stand at 20° C. overnight. The substance thereby crystallises.

Total yield: 2.0 g.
Melting point: about 190° C. (decomposition)
NMR (100 MHz; δ in d$_6$-DMSO/CD$_3$OD): 8.30 (s; thiazoline 5-H); 5.83 (d; I 5.0 Hz; 7-H); 5.18 (d; I 5.0 Hz; 6-H); 5.08 and 4.80 (AB; I 13 Hz; 3-CH$_2$-O); 3.68 and 3.55 (AB; I 18 Hz; 2-CH$_2$); 3.30 ("s"; —CH$_2$—CH$_2$—); 2.04 (s; —CO—CH$_3$); and 1.50 (s; (CH$_3$)$_3$—C).

EXAMPLE 5

7-[2-(2-Amino-4-thiazol-4-yl)-N-(imidazolidin-2-on-1-yl)-2-iminoacetamido]-3-acetoxymethyl-3-cephem-4-carboxylic acid

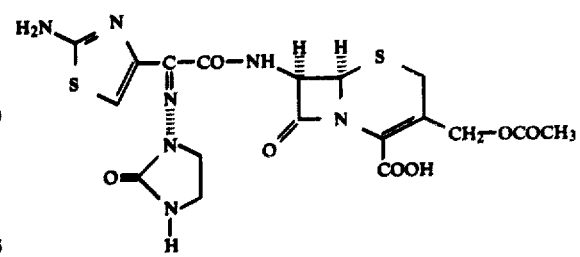

2.0 ml of anisole are added to 0.8 g of the substance prepared according to example 4 and, after cooling the mixture to 0° C. to 5° C., 12 ml of trifluoroacetic acid are added. The mixture is stirred at the same temperature for 1 hour and then poured into a mixture of ether and petroleum ether (8:2). A fine precipitate is formed. It is filtered off, washed with ether, stirred in ethyl acetate at 20° C. for 2 hours, filtered off again and dried. Yield: 0.5 g of the trifluoroacetate.

According to the NMR spectrum, the substance is a mixture of the syn- and anti-form and still contains 0.25 molar equivalent of the starting material (substance from example 4).

The ratio of the two isomeric forms (a) and (b) in the mixture is about 1 to 3 (according to the NMR spectrum).

Form (a) is concentrated in the mixture by a procedure in which the fraction corresponding to precipitate 1 in example 4 is used as the starting material for removing the protective group with trifluoroacetic acid, and this substance (0.5 g) is dissolved in 20 ml of water, the solution is covered with a layer of ethyl acetate, the pH is brought from 2.6 to 3.0 by means of sodium hydroxide solution, the mixture is stirred at 20° C. for 1 hour, a small amount of undissolved tacky substance is removed, the aqueous phase is separated off, washed twice more with ethyl acetate, brought to pH 4.5 with sodium hydroxide solution and evaporated almost completely in vacuo and the substance is precipitated by adding isopropanol, filtered off, washed with isopropanol and dried over $P_2O_5$.

Yield: 0.2 g

According to the thin layer chromatogram (Morck silica gel, butanol/ethanol/water (4:1:2)), this substance predominantly contains form (a).

IR spectrum (Nujol; carbonyl range) 1,755, 1,715, 1,650–1,600 broad adsorption and 1,520 $cm^{-1}$.

The two forms are separated by high pressure liquid chromatography.

NMR (ppm, 60 MHz, $CD_3OD$): form (a), as the Na salt: 6.95 (s, thiazoline 5-H); form (b), as the Na salt; 6.65 (s, thiazoline 5-H).

Compared with form (b), form (a) is eight times more active against E. coli 183/58.

EXAMPLE 6

1-Furylideneimino-2-oxo-3-hydrazinocarbonylimidazolidine

A mixture of 3.45 g of hydrazine hydrate and 21 ml of 50% strength aqueous methanol is warmed to 60° C. 3.0 g of 1-furylideneimino-2-oxo-3-chlorocarbonyl imidazolidine are then introduced in many small portions in the course of 100 minutes, whilst stirring. After 3 hours, the precipitate is filtered off, washed and dried.

Yield: 1.7 g, melting point: 200° C.

In the thin layer chromatogram, the substances gives only one spot.

EXAMPLE 7

2-(2-tert.-Butoxycarbonylimino-4-thiazolin-4-yl)-N-[(1-furylideneimino-2-oxo-imidazolidin-3-yl)-carbonylamino]-2-iminoacetic acid 1.5 g of the substance prepared according to example 6 are warmed to 40°–50° C. with 1.7 g of the substance prepared according to example 2 in 25 ml of ethanol for 6 hours. The precipitate is filtered off and dried.

Yield: 2.4 g.

Melting point: 205° C. (decomposition)

EXAMPLE 8

7-{2-(2-tert.-Butoxycarbonylimino-4-thiazolin-4-yl)-N-[(1-furylideneamino-2-oxo-imidazolidin-3-yl)-carbonylamino]-2-iminoacetamido}-3-acetoxymethyl-3-cephem-4-carboxylic acid

Mixture A 1.5 g of the substance prepared according to example 7 are suspended in 20 ml of methylene chloride. 0.42 ml of triethylamine and 0.02 ml of 3-dimethylaminopropanol are added. The mixture is stirred at 20° C. for 45 minutes. It is then cooled to −45° C. and 0.29 ml of chloroformic acid ethyl ester and 20 ml of acetone are added. The mixture is then stirred at −25° C. for 200 minutes.

Mixture B 1.1 g of 7-aminocephalosporanic acid are dissolved in 10 ml of water with just the amount of 1 N sodium hydroxide solution required. 10 ml of acetone are then also added. The mixture is cooled to −5° C.

Mixture A and mixture B are combined. The resulting mixture is stirred and the temperature is allowed to come slowly to 20° C. After 3 hours, the mixture is diluted with water, the pH is brought to 7.5 by means of sodium hydroxide solution, the mixture is shaken thoroughly with a large amount of ethyl acetate, a small amount of unreacted 7-aminocephalosporanic acid is removed and the aqueous phase is separated off, covered with a fresh layer of ethyl acetate and acidified to pH 1.5 with dilute hydrochloric acid, whilst stirring. After drying and stripping off the ethyl acetate solution, the substance remains, as the free acid.

Yield: 0.2 g.

According to the thin layer chromatogram, the substance contains some starting material prepared according to example 7.

EXAMPLE 9

7-{2-(2-Amino-4-thiazol-4-yl)-N-[(1-furylideneamino-2-oxoimidazolidin-3-yl)-carbonylamino]-2-iminoacetamido}-3-acetoxymethyl-3-cephem-4-carboxylic acid:

0.2 g of the substance prepared according to example 8 is left to stand with 1.0 ml of anisole and 4.0 ml of trifluoroacetic acid at 0° C.–5° C. for 15 hours.

The volatile constituents are stripped off under a high vacuum and the residue is treated with ether and filtered off. Yield: 0.2 g.

NMR (ppm, 60 MHz, $d_6$-DMSO+$CD_3OD$): 1.95 (3H, S, $CH_3CO$); 3.35–4.1 (6H, m, 2—$CH_2$, —$CH_2$—$CH_2$); 5.1 (1H, d, 6—CH); 5.75 (1H, d, 7—CH); 6.4–6.6 (1H, m 4-furane); 6.8 (1H, d, 3-furane); 6.95 (1H, s, thiazoline 5-H); and 7.7 (2H, s, broad, furane 5-H, —CH—N—).

EXAMPLE 10

7-[2-(2-tert.-Butoxycarbonylimino-4-thiazolin-4-yl)-2-oxoacetamido]-3-acetoxymethyl-3-cephem-4-carboxylic acid 2.7 g of 2-(2-tert.-butoxycarbonylimino-4-thiazolin-4-yl)-glyoxylic acid containing one molar equivalent of crystal alcohol are activated with a total of 2 ml of chloroformic acid ethyl ester (added in 3 portions) in 40 ml of methylene chloride at −30° C. in the presence of 2.8 ml of triethylamine and 2 drops of 3-dimethylaminopropanol, and the mixture is then combined with a solution of 3.6 g of 7-aminocephalosporanic acid in a mixture of 40 ml of methylene chloride and 3.6 ml of triethylamine. The resulting mixture is then allowed to come to 20° C., after 2 hours the methylene chloride is stripped off, the aqueous solution which remains is washed with ethyl acetate, then acidified (pH 1.5) and extracted with ethyl acetate and the dried organic phase is evaporated in vacuo. The residue is washed with methylene chloride and dried.

Yield: 1.8 g

NMR (60 MHz; δ in $CD_3OD$): 8.35 (s, thiazoline 5-H)

Some of the substance no longer contains butoxycarbonyl protective groups. The next reaction stage is thus partly anticipated.

EXAMPLE 11

7-[2-(2-Imino-4-thiazolin-4-yl)-2-oxoacetamido]-3-acetoxymethyl-3-cephem-4-carboxylic acid A solution of 1.25 g of the substance prepared in example 10 in 20 ml of trifluoroacetic acid is left to stand at 20° C. for 1 hour, then either the trifluoroacetic acid is stripped off and the residue is treated with ether, or a large amount of ether is added to the reaction mixture. The precipitate obtained is filtered off and washed thoroughly with methylene chloride.

Yield: 0.8 g

NMR (60 MHz; δ in $CD_3OD$): 8.20 (s; thiazoline 5-H).

EXAMPLE 12

7-[2-(2-Imino-4-thiazolin-4-yl)-N-(imidazolidin-2-on-1-yl)-2-iminoacetamido]-3-acetoxymethyl-3-cephem-4-carboxylic acid A solution of 2.0 g of 7-[2-(2-imino-4-thiazolin-4-yl)-2-oxoacetamido]-3-acetoxymethyl-3-cephem-4-carboxylic acid and 0.35 g of 1-aminoimidazolin-2-one in 60 ml of 80% strength aqueous tetrahydrofurane is left to stand at 20° C. overnight and filtered and the filtrate is diluted with water. The solution is then washed with ethyl acetate and the aqueous phase is acidified (pH 1.5) with dilute hydrochloric acid and extracted again by shaking with ethyl acetate. The aqueous phase is then neutralised with dilute sodium hydroxide solution and subsequently freezedried.

Yield: 2.1 g (according to analysis, the substance contains 5.1 molar equivalents of NaCl)

NMR (60 MHz; δ in $D_2O$): 7.00 (s, thiazoline 5-H)

After purifying by chromatography of the sodium salt on silica gel, in the thin layer chromatogram (microbiological development; test germ: E.coli Neumann) the substance exhibits only one spot, which has the same size and position, at the same dosage, as the substance described in example 5 (form (a)).

EXAMPLE 13

2-(2-Chloroacetylimino-4-thiazolin-4-yl)-acetic acid ethyl ester

After cooling to 10° C., 44.4 ml of chloroacetic anhydride are added to a solution of 40 g of 2-(2-aminothiazol-4-yl)-acetic acid ethyl ester in a mixture of 400 ml of methylene chloride and 54 ml of pyridine. The temperature increases to about 20° C. After about 30 minutes, a precipitate separates out. It is filtered off and washed with methylene chloride.

Yield: 30.6 g

Melting point: 141°–42° C.

A further 16.1 g of substance (with the same melting point) can also be isolated from the mother liquor.

EXAMPLE 14

2-(2-Chloroacetylimino-4-thiazolin-4-yl)-glyoxylic acid ethyl ester

A mixture of 200 g of the substance described in example 13 and 1,400 ml of dioxane are added to a solution, warmed to 50° C., of 160 g of selenium dioxide, 700 ml of dioxane and 31 ml of water. The mixture is boiled under reflux for 19 hours. After cooling to 40° C., the selenium is filtered off, the mother liquor is diluted with water, most of the dioxane is removed in vacuo and the substance is then taken up in a large amount of ethyl acetate. The washed and dried ethyl acetate solution is then concentrated on a rotary evaporator and the residue is recrystallised from methanol.

Yield: 82.8 g

Melting point: 169°–170° C.

IR spectrum (Nujol) (carbonyl range): 1,730; 1,700; 1,680; and 1,540 $cm^{-1}$.

EXAMPLE 15

2-(2-Chloroacetylimino-4-thiazolin-4-yl)-glyoxylic acid

A suspension of 18.5 g of the substance from example 14 in a mixture of 750 ml of ethanol and 300 ml of water is converted into a solution by warming for a short time and cooling. 134 ml of 1 N sodium hydroxide solution are then added to this mixture at 23° C., and the mixture is left to stand for 10 minutes. Evaporating off of the alcohol in a rotary evaporator is then started. After 15 minutes, the procedure is interrupted, the pH is adjusted to 7.5 with dilute hydrochloric acid and the remainder of the alcohol is removed by evaporation on a rotary evaporator. The residue is then extracted by shaking with ethyl acetate and the aqueous phase, which has been separated off, is acidified (pH 1.5) with dilute hydrochloric acid. The substance which thereby crystallises out is filtered off, washed and dried at 100° C. in vacuo for 2 hours.

Yield: 13.9 g

Melting point: about 217° C. (decomposition)

NMR (100 MHz; δ in $CD_3OC/d_6$-DMSO): 8.38 (s; thiazoline 5-H).

EXAMPLE 16

2-(2-Chloroacetylimino-4-thiazolin-4-yl)-N-(imidazolin-2-on-1-yl)-2-iminoacetic acid 2.0 g of the substance prepared in example 15 and 0.81 g of 1-aminoimidazolin-2-one are warmed for a short time in 50 ml of ethanol and the solution is then left to stand at 20° C. for 3 days. The substance is then filtered off and dried at 60° C. in vacuo.

Melting point: about 260° C. (decomposition)
The substance is a mixture of the syn- and antiforms.
NMR (100 MHz; δ in CD₃OD/d₆-DMSO): 7.27 s and 7.32 s (thiazoline 5-H).

EXAMPLE 17

6-[2-(2-Chloroacetylimino-4-thiazolin-4-yl)-N-(imidazolidin-2-on-1-yl)-2-iminoacetamido]-penicillanic acid 2.2 g of the acid described in example 16 are activated with 0.63 ml of chloroformic acid ethyl ester in a mixture of 50 ml of methylene chloride and 0.92 ml of triethylamine in the presence of 0.03 ml of 3-dimethylaminopropanol at −40° C. This solution is then combined with a solution, cooled to 0° C., of 1.86 g of 6-aminopenicillanic acid in aqueous acetone (dissolved with 1 N sodium hydroxide solution) and, after removing the cooling bath, the mixture is stirred for 3 hours. It is then diluted with a large amount of water and extracted by shaking with ethyl acetate and the aqueous phase is separated off and, after covering with a fresh layer of ethyl acetate, then acidified to pH 1.5, whilst stirring. The organic phase is then separated off, washed, dried and concentrated on a rotary evaporator. A precipitate thus separates out. It is filtered off and dried.

Yield: 1.5 g

NMR (100 MHz; δ in CD₃OD): 7.35 (s; thiazoline 5-H), 4.3 (2 H, s, Cl—CH₂—), 3.3 (4 H, pseudo-s, imidazolidinone)

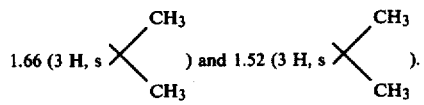

EXAMPLE 18

6-[2-(2-Imino-4-thiazolin-4-yl)-N-(imidazolidin-2-on-1-yl)-2-iminoacetamido]-penicillanic acid A mixture of 1.0 g of the substance prepared in example 17 and 5 ml of dimethylformamide, 0.78 ml of triethylamine and 0.22 g of thiourea is stirred at 20° C. for 20 hours. The triethylamine hydrochloride which has separated out is then filtered off and the reaction product is precipitated, as an oil, from the filtrate with ether. The supernatant liquor is poured off from the oil and the oil is treated with isopropanol. During this treatment, it becomes pulverulent. The precipitate is filtered off and then dissolved in water and the aqueous solution is acidified (pH 2.0). The precipitate which thus separates out is filtered off, washed with water and dried.

Yield: 0.5 g

IR spectrum (Nujol; carbonyl range): 1,760; 1,715, 1,650 −30 and 1,540 cm⁻¹.

NMR (60 MHz; δ in CD₃OD/d₇-DMS): 7.3 (s; thiazoline 5-H).

EXAMPLE 19

7-[2-(2-Imino-4-thiazolin-4-yl)-N-(imidazolidin-2-on-1-yl)iminoacetamido]-3-acetoxymethyl-3-cephem-4-carboxylic acid 2.6 g of a substance prepared according to example 4 are left to stand in 50 ml of trifluoroacetic acid at room temperature for 1 hour. About 300 ml of ether are then added, whilst cooling with ice/water, and the precipitate which has separated out is washed thoroughly with ether and dried.

Yield: 2.1 g

According to the NMR spectrum, the ratio of form a to form b (see example 5) is 1 to 0.6.

EXAMPLE 20

1-Amino-2-oxo-3-methylimidazolidine

This substance is obtained by nitrosating 1-methyl-2-oxo-imidazolidine in aqueous sulphuric acid and subsequently reducing the nitrosation product with zinc dust. Boiling point (0.2 mm Hg): 77°-84° C.

EXAMPLE 21

2-(2-tert.-Butoxycarbonylimino-4-thiazolin-4-yl)-N-(3-methylimidazolidin-2-on-1-yl)-2-iminoacetic acid 13.1 g of 2-(2-tert.-butoxycarbonylimino-4-thiazolin-4-yl)-glyoxylic acid are dissolved in 160 ml of ethanol by warming for a short time. 5.5 g of 1-amino-2-oxo-3-methyl-imidazolidine are added to this solution at 20° C. After standing overnight, the reaction mixture is evaporated in a rotary evaporator, the residue is treated with water and the precipitate is filtered off. Excess NaHCO₃ solution is added to this precipitate and the undissolved material is filtered off. The filtrate is acidified and the precipitate which separates out is filtered off, washed with water and dried.

Yield: 11.3 g

Melting point: from about 135° C. (decomposition).

NMR (60 MHz; δ in CD₃OD): 7.2 (s, thiazoline 5-H), 3.4 (pseudo-s, —CH₂—CH₂) and 2.9 (s, CH₃—N)

EXAMPLE 22

7-[2-(2-tert.-Butoxycarbonylimino-4-thiazolin-4-yl)-N-(3-methylimidazolidin-2-on-1-yl)-2-iminoacetamido]-3-acetoxymethyl-3-cephem-4-carboxylic acid

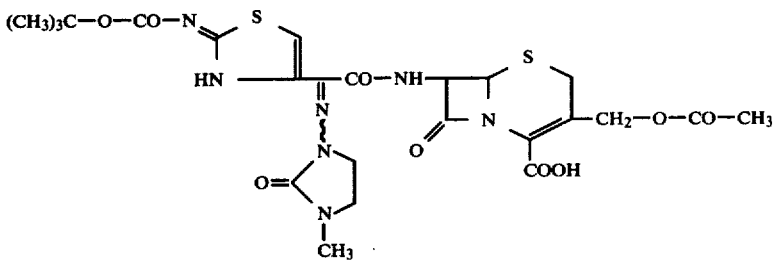

Mixture A 0.05 ml of 3-dimethylaminopropanol and 0.52 ml of chloroformic acid ethyl ester are added to a solution, cooled to −40° C., of 1 g of the product from example 21 in a mixture of 30 ml of methylene chloride and 0.75 ml of triethylamine.

Mixture B 0.814 g of 7-aminocephalosporanic acid is dissolved in a mixture of 20 ml of methylene chloride and 1 ml of triethylamine, whilst cooling with ice-water. Mixture B is then added to mixture A and the resulting mixture is stirred at 20° C. for 2.5 hours. The reaction mixture is diluted with water and extracted by shaking twice, at pH 7.5, with ethyl acetate. The aqueous phase is covered with a fresh layer of ethyl acetate and acidified to pH 2. The organic phase is separated off, dried and evaporated in vacuo and the residue is treated with ether. The precipitate is filtered off and dried.

Yield: 1.15 g

NMR (60 MHz; δ in CD$_3$OD): 7.18 (s, thiazoline 5-H) and 2.9 (s, CH$_3$—N).

EXAMPLE 23

7-[(2-Imino-4-thiazolin-4-yl)-N-(3-methylimidazolin-2-on-1-yl)-2-iminoacetamido]-3-acetoxymethyl-3-cephem-4-carboxylic acid

Mixture A 3.60 g of the substance prepared according to example 3 are suspended in 40 ml methylene chloride. 1.4 ml of triethylamine are then added at 20° C. The mixture is stirred about 10 minutes and then cooled to −40° C., and 0.05 ml of 3-dimethylaminopropanol and 0.97 ml of chloroformic acid ethyl ester are added to the solution. The mixture is stirred at −40° C. for 25 minutes and then, the mixture is cooled to −60° C.

Mixture B 3.65 g of 7-amino-3-(1-methyltetrazol-5-yl-thiomethyl)-3-cephem-4-carboxylic acid are suspended in 40 ml methylenechloride.

4.2 ml of triethylamine are added and the mixture is cooled to 0° C.

Mixture B is added to mixture A and the resulting mixture is cooled to −60° C. Afterwards the mixture is stirred at 20° C. for 3¾ hours. It is then diluted with water, the methylen chloride is stripped off, the aqueous

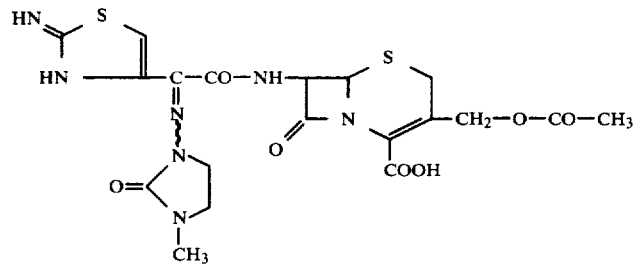

4 ml of trifluoroacetic acid are added to 0.3 g of the product from example 22, whilst cooling with ice. The mixture is left to stand at 0° to 5° C. overnight and the trifluoroacetic acid is then stripped off in a rotary evaporator. The oily residue is triturated with ether and the precipitate is filtered off, washed with ether and dried.

Yield: 0.3 g of the trifluoroacetate.

According to the NMR spectrum, the substance is a mixture of the syn- and anti-form.

NMR (ppm, 60 MHz, CD$_3$OD-d$_6$-DMSO): 6.8 and 6.87 (s, thiazoline 5-H) and 2.85 (s, CH$_3$N).

Among the new β-lactam salts of the invention, those salts that are pharmaceutically acceptable are particularly important and are preferred.

The new free β-lactam compounds of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

EXAMPLE 24

7-[2-(2-tert.-Butoxycarbonylimino-4-thiazolin-4-yl)-N-(imidazolidin-2-on-1-yl)-2-iminoacetamido]-3-(1-methyltetrazol-5-yl-thiomethyl)-3-cephem-4-carboxylic acid.

solution which remains is washed with ethyl acetate, then acidified (pH 2) and extracted with ethyl acetate and the dried organic phase is evaporated in vacuo to a little volume (about 200 ml). A yellow precipitate was filtered off, washed with ethyl acetate and dried.

Yield: 2.3 g

IR spectrum (Nujol; carbonyl range) 1770,1710 and 1540 cm$^{-1}$.

NMR(60 MHZ; CD$_3$OD/CDCl$_3$) 7.15 (s, Thiazolin 5-11), 4.0 (s. CH$_3$-Tetrazol).

EXAMPLE 25

7-[2(2-Aminothiazol-4-yl)-N-(imidazolidin-2-on-1-yl)-2-iminoacetamido]-3-(1-methyltetrazol-5-yl-thiomethyl)-3-cephem-4-carboxylic acid. The mixture of 1.5 g of the substance prepared according to example 24 and 30 ml trifluoacetic acid is allowed to stand at 20° C. for 45 minutes. The mixture is poured into 300 ml ether. The precipitate is filtered off, washed with ether and dried.

Yield: 1.15

IR spectrum (Nujol; carbonyl range) 1770, 1720, 1670 and 1540 cm$^{-1}$.

MIC ( Prot.vulg.1017): 4 μg/ml

EXAMPLE 26

2-Phenyl-N-(imidazolidin-2-on-1-yl)-2-iminoacetic acid 1.5 g Phenylglyoxylic acid is dissolved in 25 ml of 50% aqueous ethanol 1.0gl-amino-2-oxoimidazolidine are added to this solution and the mixture is then stirred at 20° C. overnight. The precipitate is filtered off, washed with ethanol and dried.

Yield: 2.2 g

Melting point: about 190° C. (decomposition)
NMR/60 MHz; d6-DMSO): 7.6–7.2(m; phenyl); 3.4–2.8 (m:—CH2—CH2—).

EXAMPLE 27

7-[2-Phenyl-N-(imidazolidin-2-on-1-yl)-2-iminoacetamido]-3-acetoxymethyl-3-cephem-4-carboxylic acid

Mixture A 2,0 g of the substance prepared according to example 26 are suspended in 40 ml methylene chloride. 1,19 ml of triethylamine are then added at 20° C. The mixture is stirred for about 10 minutes and then cooled to −20° C., and 0,05 ml of 3-dimethylaminopropanol and 0,82 ml of chloroformic acid ethyl ester are added to the solution. The mixture is stirred at −20° C. for a further 60 minutes.

MIXTURE B 2,33 of 7-aminocephaloporanic acid are suspended in 50 ml of methylene chloride at 0° C. 2,36 ml of triethylamine are added. Mixture B is then added to mixture A and the resulting mixture is stirred at 20° C. for 4 hours. The reaction mixture is diluted with water and extracted by shaking twice at pH 7,0, with ethyl acetate. The aqueous phase is covered with a fresh layer of ethyl acetate and acidified to pH 2. The organic phase is separated off, dried and evaporated in vacuo and the residue to treated with ether. The precipitate is filtered off and dried.

Yield: 2,2 g (anti-form?)
NMR (60 MHz; CD3OD): 7,5–7,2 (m; phenyl); 5,75 (d; 7—H); 2,05 (s;—O—CO—CH3).
IR Spectrum (Nujol): 1770 cm$^{-1}$ ($\beta$-lactam)
MIC (E/ml) E.col. 183/58:8-16

EXAMPLE 28

2-Phenyl-N-(imidazolidin-2-on-1-yl)-2-iminoacetic acid chloride 5,0 g of the substance described in example 26 is suspended in 100 ml of methylene chloride and the solution of 4,05 ml thionylchloride in 20 ml methylene chloride are added. The mixture is stirred overnight. The precipitate is filtered off, washed with methylene chloride and dried.

Yield: 1,75 g
Melting point: about 125° C. (decomposition)
IR-spectrum (Nujol): 1805 cm$^{-1}$ (-COCl)

EXAMPLE 29

7-[2-Phenyl-N(imidazolidin-2-on-1-yl)-2-iminoacetamido]-3-acetoxymethyl-3-cephem-4-carboxylic acid 1,08 g 7-aminocephalosporanic acid are suspended in 20 ml of methylene chloride. 1,0 ml of triethylamine are added. The mixture is stirred at 0° C. for 5 minutes. To this solution 1 g of the substance described in example 28 are added. The mixture is stirred at 20° C. for 3 hours. The reaction mixture is diluted with water and extracted by shaking with ethyl acetate. The aqueous phase acidified at pH 2 and then extracted three times with ethyl acetate. The organic phase is separated off, dried and evaporated in vacuo and the residue is treated with ether. The precipitate is filtered off and dried (yield 2,2 g). The solution of this substance in a 5% aqueous NaHCO3 as acidified to pH 2. The precipitate is filtered off, washed with water and dried.

Yield: 0,6 g (syn-form?)
NMR (60 MHZ; CD3OD): 6,0 (d; 7—H); 2,05 (s;—O—CO—CH3).
IR spectrum (Nujol): 1770 cm$^{-1}$ ($\beta$-lactam)
MIC (E/ml):
E. Col. 183/58:$\leq$0,25

EXAMPLE 30

7-[2-(2-tert.-Butoxycarbonylimino-4-thiazolin-4-yl)-N-(imidazolidin-2-on-1-yl)-2-iminoacetamido]-3-[(2-methyl-1,3,4-thiadiazol-5-yl)-thio-methyl]-3-cephem-4-carboxylic acid

MIXTURE A 1,9 g of the substance prepared according to example 3 are suspended in 40 ml methylene chloride. 0,8 ml of triethylamine are then added. The mixture is cooled to −40° C. and 5 drops of 3-dimethylaminopropanol and 0,53 ml of chloroformic acid ethyl ester are added. The mixture is stirred for 25 minutes and cooled to −60° C.

Mixture B 2,0 g of 7-amino-3-(2-methyl-1,3,4-thiadiazol-5-yl-thio-methyl)-3-cephem-4-carboxylic acid are suspended in the mixture of 40 ml methylene chloride and 2,4 ml triethylamine are added and the mixture is cooled to 0° C. Mixture B is added to mixture A and the resulting mixture is cooled to −60° C. Afterwards the mixture is stirred at 20° C. for 3,5 hours. It is then diluted with water, the methylene chloride is stripped off, the aqueous solution is washed with ethylacetate, then acidified (pH 1,8) and extracted with ethyl acetate and the dried organic phase is evaporated in vacuo to a little volume. The precipitate was filtered off and dried.

Yield: 1,4 g
IR spectrum (Nujol): 1770, 1720, 1550 cm$^{-1}$.

EXAMPLE 31

7-[2-(2-Aminothiazol-4-yl)-N-(imidazolidin-2-on-1-yl)-2-iminoacetamido]-3-[(2-methyl-1,3,4-thiadiazol-5-yl)-thiomethyl]-3-cephem-4-carboxylic acid The mixture of 0,7 g of the substance prepared according to example 30 and 14 ml trifluoroacetic acid is allowed to stand at 20° C. for 45 minutes. The mixture is poured into 140 ml ether. The precipitate is filtered off, washed with ether and dried.

Yield: 0,7 g
IR spectrum (Nujol; carbonyl range) 1770($\beta$-lactam CO), 1710, 1650 and 1550 cm$^{-1}$.
MIC (E. Coli T 7)=0.25 E/ml

EXAMPLE 32

7-[2-(2-tert.-Butoxycarbonylimino-4-thiazolin-4-yl)-N-[imidazolidin-2-on-1-yl)-2-iminoacetamido]-3-[(2-methyl-1,3,4-oxdiazol-5-yl)-thio-methyl]-3-cephem-4-carboxylic acid.

Mixture A 1,9 g of the substance prepared according to example 3 are suspended in 40 ml methylene chloride and 0,8 ml of triethylamine are added. The mixture is cooled to −40° C. and 5 drops of 3-dimethylaminopropanol and 0,53 ml of chloroformic acid ethyl ester are added. The mixture is stirred for 25 minutes and then cooled to −60° C.

Mixture B 2 g of 7-amino-3-(2-methyl-1,3,4-oxdiazol-5-yl-thiomethyl)-3-cephem-4-carboxylic acid are suspended in 40 ml methylene chloride. After cooling to 0° C., 2,4 ml triethylamine are added. Mixture B is added to mixture A and the resulting mixture is cooled to −60° C. Afterwards the mixture is stirred at 20° C. for 3 hours. It is then diluted with water, the methylene chloride is stripped off, the aqueous solution is washed with ethyl acetate, then acidified (pH 1,8) and extracted with ethyl acetate. The dried organic phase is evaporated in vacuo to a little volume. The precipitate was filtered off and dried.

Yield: 2,3 g

IR spectrum (Nujol; carbonylrange): 1780, 1720 and 1530 cm$^{-1}$.

EXAMPLE 33

7-[2(2-Aminothiazol-4-yl)-N-(imidazolidin-2-on-1-yl)-2-iminoacetamido]-3-[(2-methyl-1,3,4-oxdiazol-5-yl)-thiomethyl]-3-cephem-4-carboxylic acid. The solution of 1,0 g of the substance prepared according to example 32 in 20 ml trifluoroacetic acid is allowed to stand at 20° C. for 45 minutes. The mixture is poured into 200 ml ether. The precipitate is filtered off, washed with ether and dried.

Yield: 0,9 g

IR spectrum (Nujol; carbonyl range): 1770, 1715, 1650, 1625 cm$^{-1}$.

MIC (E.coli Neumann) ≦1 E/ml

In the same way it is possible to synthesize:

7-[1(2-Aminothiazol-4-yl)-N-(imidazolidin-2-on-1-yl)-2-imino acetamido]-3-amino carbonyloxymethyl-3-cephem-4-carboxylic acid.

What is claimed is:

1. A β-lactam of the formula

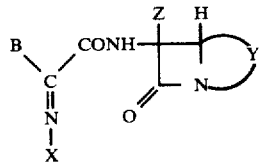

in which

B is

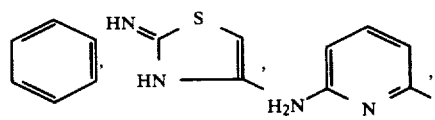

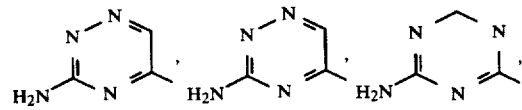

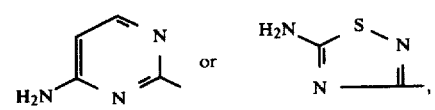

Z is a hydrogen atom or a $C_1$ to $C_4$ alkoxy group, Y is

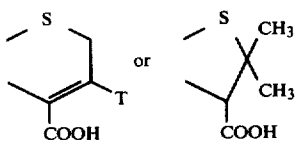

T is —CH$_2$—O—CO—CH$_3$, —CH$_2$—S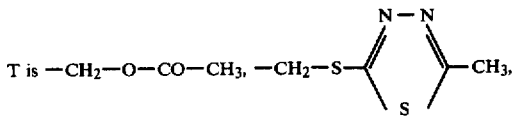

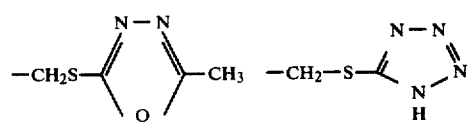

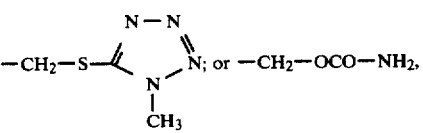

X is 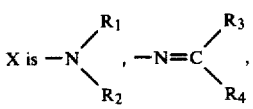

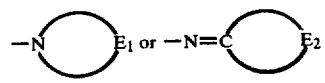

R$_1$, R$_2$, R$_3$ and R$_4$ each independently is a hydrogen atom; an alkyl, alkenyl or alkinyl radical with up to 4 carbon atoms; an alkadienyl, cycloalkenyl or cycloalkadienyl radical with up to 7 carbon atoms; a cycloalkyl radical with up to 6 carbon atoms; phenyl; or

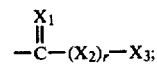

X$_1$ and X$_2$ each independently is O, S or N—X$_3$,

X$_3$ is an alkyl or alkenyl radical with up to 4 carbon atoms; a cycloalkyl radical with up to 7 carbon atoms; phenyl; C$_{1-4}$-alkylphenyl; C$_{1-4}$-alkoxyphenyl; halophenyl; thienyl; thiazolyl; pyridyl; pyrrolidin-2-on-1-yl; imidazolidin-2-on-1-yl; piperazine-2,3-dion-1-yl; 1-furylidene amino-2-oxy-imidazolidin 1-yl; or —SO$_2$—X$_4$;

r is 0 or 1;

X$_4$ is C$_{1-4}$-alkyl, phenyl, NH$_2$, mono- or di-alkylamino or hydroxyl;

E$_1$ is —(CO)$_m$—(NR$_9$)$_m$—(CH$_2$)$_n$—, —(CH$_2$)$_m$—R$_1$-O—(CH$_2$)$_m$—, —(CO)$_m$—(CH$_2$)$_p$—, —(CO)-2—$_m$—(CH$_2$)$_n$—(CO)$_m$—, —CO—CH═CH—CO——CO—O—(CH$_2$)$_q$—, —CO——S—(CH$_2$)$_q$—, —CO—NR$_9$—CO—(CH$_2$)$_m$—, —SO$_2$—(CH$_2$)$_p$—, —CO—(CH$_2$)$_q$—SO$_2$—, —CO—NR$_9$—N═CH—, —(CH═CH)$_2$—, —CO—NH—N═CH—CO— or —CO—(CH═CH)$_2$—;

R$_9$ has any of the meanings given for R$_1$ or is

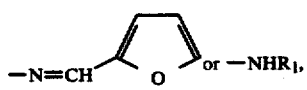

$R_{10}$ is O, S, SO, $SO_2$ or $NR_{11}$, $R_{11}$ is a hydrogen, methyl, ethyl, cyclopropyl, methylsulphonyl or furylideneamino radical, m is 1 or 2, n is 2 or 3, p is 3, 4 or 5, q is 2, 3 or 4, and $E_2$ together with the carbon atom forms a 4- to 7-membered carbocyclic ring or heterocyclic ring containing 1 or 2 oxygen, sulfur or nitrogen atoms as hetero-atoms.

2. A compound according to claim 1, in which X is

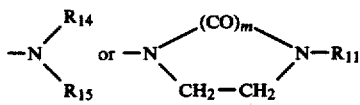

$R_{11}$ denotes a hydrogen atom or a methyl, ethyl, cyclopropyl, methylsulphonyl or furylideneamino radical, $R_{14}$ denotes a hydrogen atom or a $C_1$ to $C_4$ alkyl, benzyl, phenethyl, cyclohexyl or phenyl radical or a heterocyclic radical of the formula

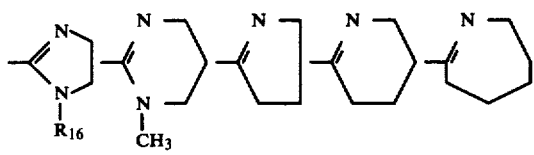

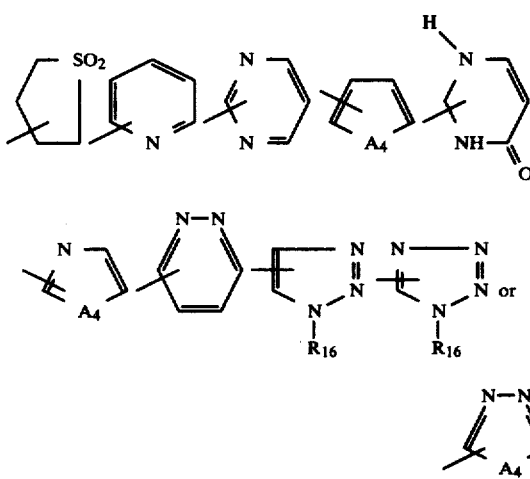

$R_{16}$ denotes a hydrogen atom or a $C_1$ to $C_4$ alkyl, hydroxyethyl or $C_1$ to $C_4$ alkoxyethyl radical, $A_4$ denotes O or S, and $R_{15}$ denotes a hydrogen atom or a $C_1$ to $C_4$ alkyl, ($C_1$ to $C_4$ alkyl)-carbonyl or phenylcarbonyl radical.

3. A compound according to claim 1, in which

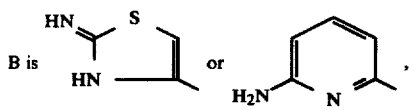

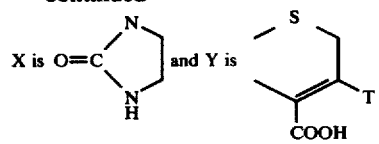

4. A compound according to claim 1, in which

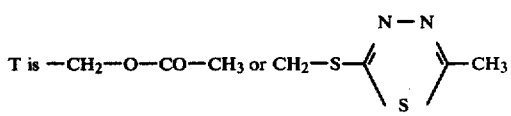

5. A compound according to claim 1, wherein such compound is 7-[2-(amino-4-thiazol-4-yl)-N-(imidazolidin-2-on-1-yl)-2-iminoacetamido]-3-acetoxymethyl-3-cephem-4-carboxylic acid of the formula

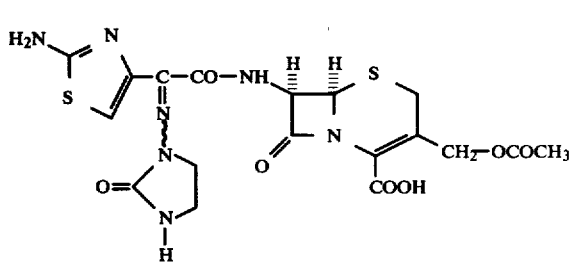

6. A compound according to claim 1, wherein such compound is 7-[2-(2-aminothiazol-4-yl)-N-(imidazolidin-2-on-1-yl)-2-iminoacetamido]-3-[(2-methyl-1,3,4-thiadiazol-5-yl)-thiomethyl]-3-cephem-4-carboxylic acid.

7. A compound according to claim 1, wherein such compound is 7-[2(2-aminothiazol-4-yl)-N-(imidazolidin-2-on-1-yl)-2-iminoacetamido]-3-[(2-methyl-1,3,4-oxdiazol-5-yl-thiomethyl]-3-cephem-4-carboxylic acid.

8. A compound according to claim 1, wherein such compound is 7-[2(2-aminothiazol-4-yl)-N-(imidazolidin-2-on-1-yl)-2-iminoacetamido]-3-(1-methyltetrazol-5-yl-thiomethyl)-3-cephem-4-carboxylic acid.

9. A compound according to claim 1, wherein such compound is 7-[1(2-aminothiazol-4-yl)-N-(imidazolidin-2-on-1-yl)-2-imino acetamido]-3-amino-carbonyloxymethyl-3-cephem-4-carboxylic acid.

10. A pharmaceutical composition containing an antibacterially effective amount of a compound according to claim 1, in admixture with a liquid diluent other than a solvent of a molecular weight less than 200 except in the presence of a surface-active agent.

11. A pharmaceutical composition containing an antibacterially effective amount of a compound according to claim 1, in the form of a sterile or physiologically isotonic aqueous solution.

12. A composition according to claim 10 or 11, containing from 0.5 to 95% by weight of the active ingredient.

13. A medicament in dosage unit form comprising a composition according to claim 11.

14. A medicament in the form of tablets, pills, dragees, capsules, ampoules, or suppositories comprising a compound according to claim 1.

15. A method of combating bacterial diseases in human and non-human animals or for promoting growth and for improving feed utilisation in animals which comprises administering to the animals an effective amount of a compound according to claim 1.

16. A method according to claim 15, in which the active compound is administered in an amount of 5 to 1,000 mg per kg body weight per day.

* * * * *